United States Patent [19]

Popescu et al.

[11] Patent Number: 5,009,819

[45] Date of Patent: Apr. 23, 1991

[54] TASTE MODERATING COMPOSITION

[75] Inventors: Mircea C. Popescu, Plainsboro; Edgar T. Mertz, Princeton, both of N.J.

[73] Assignee: The Liposome Company, Inc., Princeton, N.J.

[21] Appl. No.: 119,667

[22] Filed: Nov. 12, 1987

[51] Int. Cl.$^5$ ............... B01J 13/02; B01J 13/04
[52] U.S. Cl. ............................... 264/4.1; 424/450
[58] Field of Search ............... 514/313; 424/450; 264/4.1

[56] References Cited

U.S. PATENT DOCUMENTS

| | | | |
|---|---|---|---|
| 4,302,459 | 11/1981 | Steck et al. | 514/962 |
| 4,416,872 | 11/1983 | Alving et al. | 514/313 |
| 4,522,803 | 6/1985 | Lenk et al. | 424/1.1 |
| 4,588,578 | 5/1986 | Fountain et al. | 424/1.1 |
| 4,721,612 | 1/1988 | Janoff et al. | 424/1.1 |
| 4,861,580 | 8/1969 | Janoff et al. | 424/1.1 |

FOREIGN PATENT DOCUMENTS

WO86/05977 10/1986 World Int. Prop. O. .

OTHER PUBLICATIONS

CA107(24):223182q.
CA107(3):17846f.
CA104(6):39720a.
CA94(16):125259g.
CA92(21):174229w.
CA92(20):169129j.
CA92(20):169128h.
CA90(26):210001k; CA Registry Entry "Chloraquine".

Primary Examiner—Theodore Morris
Assistant Examiner—David M. Brunsman
Attorney, Agent, or Firm—Allen Bloom; Thomas M. Saunders; Catherine L. Kurtz

[57] ABSTRACT

A taste moderating composition comprising a liposome associated flavorant and method of preparation and use.

1 Claim, No Drawings

TASTE MODERATING COMPOSITION

FIELD OF THE INVENTION

This invention concerns a taste moderating composition—for either suppressing or enhancing the taste of flavorants—comprising a liposome associated flavorant, and method of preparation and use. Some flavorants, often therapeutic agents are of unplesant taste, while others, such as essential oils, are desirable. The composition and method of this invention may be used to suppress the taste of unpleasant tasting lipophobic substances such as lipophobic therapeutic agents, and alternatively to enhance the taste of lipophilic substances, particularly in aqueous suspensions where the flavorant is aqueous immiscible.

BACKGROUND OF THE INVENTION

The enhancement or minimization of flavors have long been subjects of concern in the food and pharmaceutical industries. Pharmaceuticals to be administered orally are most easily administered, particularly to children, if the pharmaceutical has a flavor which is not unduly unpalatable. In the past, the administrability of formulations containing unpleasant tasting medications relied on strong tasting masking agents such as fruit flavors. These have not been totally successful, particularly with bitter therapeutic agents such as quinine. Furthermore, if the formulation tastes too candy-like it is more likely to be accidentally consumed by children. Thus there is a need for a method of avoiding or overcoming the unpalatable taste of therapeutic agents by rendering the taste neutral or more palatable and in some embodiments doing so without substituting an enticing taste therefor while in other embodiments for both reducing the tasteability of the unpleasant tasting compound and using a taste masking agent.

In the food industry enhancement of desirable tastes is an important consideration. Flavorants are expensive and sources for concern as to toxicity if present in great quantities. Frequently flavorants are lipophilic compositions such as essential oils, which are largely immiscible in aqueous substances. The industry has long required a preparation to enhance the tasteability of certain desirable flavorants, particularly in aqueous preparations such as drinks and soups, without the drawbacks of taste potentiators such as monosodium glutamate.

The instant invention provides a single composition and method of preparation and use that answers the seemingly opposed requirements of moderating flavorant by suppressing tastability in some circumstances and enhancing flavorant tastability in other circumstances.

SUMMARY OF THE INVENTION

This invention will be understood to include a taste moderating composition comprising a liposome associated flavorant, with the composition being adapted for oral administration. This includes the taste moderating composition wherein the moderation is suppression of lipophobic flavorant, the liposome being primarily absent exogenous flavorant, as well as the preferred condition of absent tastable exogenous flavorant. Such liposomes with taste suppressed lipophobic flavorant may further include a lipophilic flavorant.

In some embodiments the suppressed lipophobic flavorant is a therapeutic agent, such as a lipophobic 4-aminoquinoline, an alkaloid, an antibiotic, liquid barium, antitussives, antihistamine or analogues and derivatives thereof. The use of stable liposomes to encapsulate the therapeutic agents is particularly included. As to the specific group of 4-aminoquinoline, there is included chloraquine, hydroxychloraquine or amodiaquine.

In some embodiments of the taste suppressing liposome composition there further comprises a suitable pharmaceutical carrier.

The taste moderating composition also includes the moderation being taste enhancement of a lipophilic flavorant, such as where the flavorant is a lipophilic therapeutic agent or wherein the flavorant additionally includes a suitable pharmaceutical carrier such as aqueous suspension, such as for a food additive.

The invention also includes a method of moderating the taste of a flavorant composition by encapsulating the composition in a liposome, with the liposomal composition being adapted for oral administration.

The method of moderation includes suppression of taste in instances in which flavorant is lipophobic by removing exogenous lipophobic flavorant such that said liposome is primarily absent exogenous lipophobic flavorant, and in a prefered embodiment further comprises removing from the composition tastable exogenous lipophobic flavorant. The method further comprises encapsulating in the liposome a lipophilic flavorant.

In one embodiment of the method the flavorant is a lipophobic therapeutic agent, such as a lipophobic 4-aminoquinoline, an alkaloid, an antibiotic, liquid barium, antitussive, antihistamine or analogues and derivatives thereof. The method also includes the use of stable liposomes to encapsulate therapeutic agents. In particular the method includes antitussives as well as antihistamines, or a 4-aminoquinoline, analogues and derivatives thereof, such as chloraquine, hydroxychloraquine or amodiaquine.

The method of taste suppression includes admixing with a suitable pharmaceutical carrier, such as an aqueous pharmaceutical carrier.

The invention also includes a method of masking the taste of a substance by the process of adding to such substance a taste effective amount of a composition of enhanced flavor, said composition comprising a liposome associated lipophilic flavorant, said composition adapted for oral administration.

DETAILED DESCRIPTION OF THE INVENTION

Liposomes are completely closed lipid bilayer membranes containing an entrapped aqueous volume. Liposomes may be unilamellar vesicles (possessing a single bilaryer membrane) or multilameller vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "head" orient towards the aqueous phase.

The original liposome preparation of Bangham, et al. (J. Mol. Biol., 1965, 12:238-252) involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This technique provides the basis for the development of the small sonicated unilamellar vesicles described by Papahadjopoulos et al. (*Biochim. Biophys. Acta.,* 1968, 135:624–638), and large unilamellar vesicles.

Unilamellar vesicles may be produced using an extrusion apparatus by a method described in Cullis et al., PCT Application No. WO 87/00238, published Jan. 16, 1986, entitled "Extrusion Technique for Producing Unilamellar Vesicles" incorporated herein by reference. Vesicles made by this technique, called LUVETS, are extruded under pressure through a membrane filter.

Another class of liposomes are those characterized as having substantially equal lamellar solute distribution. This class of liposomes is denominated as stable plurilamellar vesicles (SPLV) as defined in U.S. Pat. No. 4,522,803 to Lenk, et al., monophasic vesicles as described in U.S. Pat. No. 4,558,579 to Fountain, et al. and frozen and thawed multilamellar vesicles (FATMLV) wherein the vesicles are exposed to at least one freeze and thaw cycle; this procedure is described in Bally et al., PCT Publication No. 87/00043, Jan. 15, 1987, entitled "Multilamellar Liposomes Having Improved Trapping Efficiencies" and incorporated herein by reference.

A variety of sterols and their water soluble derivatives have been used to form liposomes; see specifically Janoff et al., PCT Publication No. WO 85/04578, published Oct. 24, 1985, entitled "Steroidal Liposomes." Mayhew et al., PCT Publication No. WO 85/00968, published Mar. 14, 1985, described a method for reducing the toxicity of drugs by encapsulating them in liposomes comprising alpha-tocopherol and certain derivatives thereof. Also, a variety of tocopherols and their water soluble derivatives have been used to form liposomes, see Janoff et al., PCT Publication No. WO 87/02219, published Apr. 23, 1987, entitled "Alpha Tocopherol-Based Vesicles."

Liposomes of equal solute distribution are preferred in the practice of this invention, such as SPLVs and FATMLVs but other liposomes are suitable.

In the present invention, the term lipid as used herein shall mean any suitable material resulting in a bilayer such that a hydrophobic portion of the lipid material orients toward the interior of the bilayer while a hydrophilic portion orients toward the aqueous phase. Lipids further include highly hydrophobic compounds such as triglycerides, and sterols such as cholesterol which can be incorporated into the bilayer.

The lipids which can be used in the liposome formulations of the present invention are the phospholipids such as phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), and the like, alone or in combination. The phospholipids can be synthetic or derived from natural sources such as egg or soy. Useful synthetic phospholipids are dymyristoylphosphatidylcholine (DMPC) and dimyristoylphosphatidylglycerol (DMPG). The liposomes can also contain other steroid components such as polyethylene glycol derivatives of cholesterol (PEG-cholesterols), coprostanol, cholestanol, or cholestane, and combinations of PC and cholesterol. They may also contain organic acid derivatives of sterols such as cholesterol hemisuccinate (CHS), and the like. Organic acid derivatives of tocopherols may also be used as liposome-forming ingredients, such as alpha-tocopherol hemisuccinate (THS). Both CHS- and THS-containing liposomes and their tris salt forms may generally be prepared by any method known in the art for preparing liposomes containing these sterols. In particular, see the procedures of Janoff, et al., PCT Publication No. WO 85/04578, published Oct. 24, 1985, entitled "Steroidal Liposomes," and Janoff, et al., PCT Publication No. WO 87/02219, published Apr. 23, 1987, entitled "Alpha-Tocopherol Based Vesicles," filed Sept. 24, 1986, respectively. The liposome may also contain glycolipids.

"Flavorant" as used herein shall mean a tastable composition. This includes desirable tastes as well as undesirable tastes. Flavorants thus defined may be therapeutic agents such as quinine as well as classic food flavoring substances such as oil of wintergreen and synthetic vanilla.

"Therapeutic agents" shall be understood to include biologically active agents ("bioactive agents") to be administered orally as well as other medically useful agents to be administered orally such as contrast materials (e.g., dyes) and diagnostic materials.

"Suppression" as used in relation to flavorants shall mean a reduction in the tastability of the flavorant. Suppression will be the result of encapsulation of lipophobic substances with primary absence of exogenous flavorant. The testing of the level of suppression is necessarily a subjective test, but may be reasonably determined by testing by a sufficent population sample. The minimal concentration at which a substance in a carrier medium is detectable is a possible test for suppression, and other tests are known to those skilled in the art. Preferred, for the application of making unpalatable therepeutic agents less objectionable, is a test of the concentration at which a particular therapeutic agent becomes so unpalatable as to be deleterious to patient compliance with the required medication regimen.

The duration of the suppression of taste by liposome encapsulation will be, in part, dependent on the durability of the liposome in the oral environment. Thus if the liposome breaks down while still in the mouth the flavorant will be exposed to the taste buds. The use of "stable liposomes", liposomes made of hydrogenated or saturated lipids, will delay and reduce the incidence of breakdown prior to the passage of the flavorant from the mouth.

For stabile liposomes, hydrogenated lipids include phosphatidylethanolamine, phosphatidylglycerol, sphingomyelin, and particularly phosphatidlycholine are useful.

Within the class of stabile liposomes is a subclass of liposomes characterized as having solute distribution substantially equal to the solute distribution environment in which prepared. This subclass may be defined as stable plurilamellar vesicles (SPLV) as defined in U.S. Pat. No. 4,522,803 to Lenk et al. Other liposomes of equal solute distribution are monophasic vesicles described in U.S. Pat. No. 4,588,578 to Fountain et al. and frozen and thawed multilamellar vesicles (FATMLVs) as described in "Solute Distributions and Trapping Efficiencies Observed in Freeze-Thawed Multilamellar Vesicles" Mayer et al. *Biochimica et Biophysica Acta* 817:193–196 (1985). It is believed that the particular stability of the SPLV type liposomes arises from the low energy state attendant to solute equilibrium.

As to taste supression, it has now been determined that liposomal encapsulated lipophobic flavorant, primarily absent exogenous flavorant suppresses tasteability of the flavorant. Liposomes "primarily absent" exogenous flavorant shall be understood to have exogenous flavorant at levels not greater than about that concentration of flavorant that is minimally tastable. This limitation is a critical limitation of the suppression aspect of this invention. In the preferred embodiment exogenous flavorant not present in a tastable amount, in total, for the contemplated dosage size which will be termed "absent tasteable exogenous flavorant".

For taste suppression the liposome preparations of this invention may be washed of excess exogenous flavorant, such as a quinine, by centrifugation of the preparation for sufficient time and at sufficient velocity to cause liposomes to sediment but not to lose integrity. The supernatant is decanted and the liposomes are resuspended in saline or other aqueous media. This procedure may be repeated until sufficient exogenous flavorant is eliminated.

Other means of removing excess exogenous flavorant such as dialysis or gel filtrations are suitable and well known in the art.

Lipophobic quinine, derivatives and analogues thereof, particularly 4-aminoquinolines, are widely used therapeutic agents of well known bitter taste. Exemplary of such agents are amodiaquine, chloroquine and hydroxychloraquine. Oral preparations of liposomal quinines that are palatable to children are useful embodiments of this invention. Other unpalatable therapeutic agents which are lipophobic are alkaloids (e.g., caffeine, codine, dihydrocodeinone) antibiotics (e.g., aminoglycosides, cephlexin, sulfisoxazole, ampicillin, pivampicillin), liquid barium (actually a suspension in an aqueous phase but grouped with lipophobic substances for convenience), antitussive (dextromethorphan), antihistamines (chlortrimaton) and lipophobic vitamins (B complexes).

"Enhancement" as used in relation to flavorants shall mean an increase in the tastability of the flavorant. Enhancement will be the result of the practice of this invention with lipophilic substances. This will usually refer to a desirable taste but may include an unpalatable flavorant added to a secondary substance to cause aversion to that substance containing the unpalatable flavorant. Enhancement is tested by a number of methods known to those skilled in the art, with a minimum detectable concentration as noted by human testers being one such method.

Lipophilic flavorants (usually with a desirable taste such as menthol, or those with an undesirable taste to be used in an aversion context such as castor oil) may be rendered of enhanced tastability by the instant invention. Vegetable aromatic oils such as menthol, clove, and wintergreen have a low solubility in water, and are particularly enhanced by incorporation into liposomes. In some embodiments liposomal preparations of enhanced flavorants are added to secondary substances to flavor such substances, and potentially mask the taste of such secondary substance. For example a liposomal clove oil might be added to an unpalateble liquid to render the liquid palatable and in part mask the unpalatable taste. A sufficient amount of an enhanced taste lipophilic flavorant of this invention to accomplish the purpose of rendering a secondary substance palatable shall be termed a "taste effective" amount.

In one embodiment both the suppression of lipophobic taste and the enhancement of lipophilic taste are combined. By way of example a liposome preparation of quinine (a lipophobic flavorant), primarily absent exogenous quinine is prepared so as to also contain the lipophilic flavorant menthol. The resulting preparation both suppresses the quinine taste and benefits from the presence of menthol taste to further mask the quinine taste and improve palatability. To prepare such liposomes methods well known in the art may be used. For example in an SPLV preparation lipophilic flavorant would be added in the organic solvent phase and lipophobic flavorant in the aqueous phase.

In pharmaceutical uses, the liposomes of the present invention can be administered along but will generally be administered in admixture with a pharmaceutical carrier selected with regard to the therapeutic agent and standard pharmaceutical practice.

For the oral mode of administration, the liposomes of this invention can be used in the form of tablets, capsules, losenges, troches, powders, syrups, elixirs, aqueous solutions and suspensions, and the like. In the case of tablets, carriers which can be used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient is combined with emulsifying and suspending agents. Aqueous pharmaceutical carrieres art well known in the are and include water, isotonic saline, and buffered physiological solutions. If desired, certain sweetening and/or flavoring agents can be added. In food uses of enhancement liposomes, the carrier of choice is an aqueous carrier.

For administration to humans in the curative treatment of disease states responding to the therapeutic agent, the prescribing physician will ultimately determine the appropriate dosage for a given animal or human subject, and this can be expected to vary according to the age, weight, and response of the subject as well as the nature and severity of the subject's disease. The dosage of the therapeutic agent in liposomal form will generally be about that empolyed for the free agent. In some cases, however, it may be necesary to administer dosages outside these limits.

4-aminoquinolines such as chloroquine diphosphate are administered at dosages for children of generally about 5 mg/kg and seldom above 10 mg/kg. Unit dosages are thus from about 15 to about 125 mg for children. Adult unit doses are from about 200 to about 600 mg active ingredient.

It is clear from the foregoing that preparation of compositions of the invention in unit dosage form is a particularly advantageous application of the invention.

In enhancement applications, the strength of the desired taste will be the guide, but ideally less of the taste enhancing substance will be required to achieve a specific prominence of taste.

In therapeutic uses of taste suppression by the instant invention, preparations in unit dosage form will be of particular importance. This is in part because the recipients of such doses will in some embodiments be children. In such applications the ease of administration is particularly enhanced when a therapeutic preparation is in unit dosage form.

EXAMPLE 1

Taste Suppression: Chloroquine

Chloroquine in the form of stable plurilamellar vesicles was prepared by mixing 50 mg of egg phosphatidylcholine in 5 ml of diethyl ether and 0.3 ml of chloroquine solution (200 mg/ml in water) in a 50 ml round bottom flask. The mixture was sonicated at room temperature (18° to 20° C.) while comcomitantly evaporating the ether with a stream of nitrogen. The resulting lipid paste was resuspended in 5 ml Hepes (N-2-hydroxyethyl piperazine-N'-2-ethane sulfonic acid) buffer (pH 7.2), to form liposomes. The liposomes were washed thoroughly 4 times by centrifugation at 10,000 rpm for 10 minutes and finally resuspended in 1.5 ml of Hepes buffer.

To determine the entrapment of drug, 0.3 ml of the liposome suspension was sonicated at maximum power with a sonicator (Branson, Shelton, Ct.) equipped with metallic probe, thus disrupting the liposomes and releasing the chloroquine contents.

The released chloroquine was determined spectrophotometrically at 223 nm using a pre-established standard curve. The entrapment value was 21.5%. The final composition of this liposome foundation was as follows:

| egg phosphatidylcholine | 25 mg |
|---|---|
| Chloroquine diphosphate | 8.6 mg |
| per 1 ml of Hepes buffer | (pH 7.2) |

Tasting Test: Liposomal chloroquine, liposome prepared as above without drugs, and a control solution of chloroquine in Hepes buffer (pH 7.2) at 8.6 mg/ml were tasted by humans by applying one drop on the tongue alternatively at 1-2 minute intervals. The results were that a strong bitter taste was apparent only in the control solution. The liposomal chloroquine and the control empty liposome suspension had no bitter taste at all.

EXAMPLE 2

Taste Suppression: Quinine 0.5 ml of diethyl ether containing egg phosphatidylcholine at a concentration of 100 mg/ml and 0.3 ml quinine-HCl solution at 40 mg/ml of Hepes buffer (pH 7.2) were mixed and sonicated while evaporating the ether with a stream of nitrogen. This process and the subsequent steps in prepartion of liposomes was done as described for chloroquine liposomes Example 1. The entrapment of quinine in liposomes was 48.5%.

The final composition of quinine liposome preparation was as follows:

| egg phosphatidylcholine | 25 mg |
|---|---|
| Quinine - HCl | 5.9 mg |
| per 1 ml of Hepes buffer | (pH 7.2) |

Tasting Test: This was done as described for liposomal chloroquine in Example 1 using as control a quinine solution at 5.9 mg/ml Hepes buffer (pH 7.2) and empty liposomes (no drug) prepared from egg phosphatidylcholine. The results were that the bitter taste of quinine was partially suppressed by entrapment in liposomes. Empty liposomes were tasteless.

EXAMPLE 3

Taste Enhancement: Menthol 5 mg menthol powder (Sigma, St. Louis, Mo.) and 100 mg egg phosphatidylcholine powder (Sigma) were dissolved in 5 ml ether. This mixture was placed in a 50 ml round bottom flask containing 0.3 ml water and used to prepare liposomes as described in Example 1. In this example the resulting liposomes, after washing were resuspended in water.

The final composition of menthol liposome preparation was as follows:

| egg phosphatidylcholine | 100 mg |
|---|---|
| menthol | 5 mg |
| in 1 ml double distilled water | |

Tasting test: This was done as described in Example 1 except that the controls were (a) saturated menthol solution in water at room temperature (18°-20° C.), and (b) liposomes containing the above solution (no additional menthol) and resuspended in water at 100 mg PC/ml. The taste results were that the menthol flavor was enhanced in the liposomal menthol preparation over the control menthol preparation, and the empty control was tasteless.

What is claimed is:

1. A method of making palatable an unpalatable hydrophobic therapeutic agent for oral administration which comprises:

forming liposomes in the presence of said hydrophobic agent, a solvent and a hydrophilic flavoring agent, to encapsulate a portion of said hydrophobic agent separating said liposomes from unencapsulated agent and solvent by multiple washing and centrifuging steps that remove exogenous flavoring agent from said liposomes but do not reduce the stability of the liposomes and adding a pharmaceutical carrier to said liposomes for oral administration.

* * * * *